US008728395B2

(12) United States Patent
Suzuki et al.

(10) Patent No.: US 8,728,395 B2
(45) Date of Patent: May 20, 2014

(54) AUTOMATIC ANALYZER

(75) Inventors: Kouichi Suzuki, Hitachinaka (JP);
Hiroshi Watanabe, Hitachinaka (JP);
Takeshi Shibuya, Hitachinaka (JP);
Shinichi Nagara, Mito (JP)

(73) Assignee: Hitachi High-Technologies Corporation, Tokyo (JP)

(*) Notice: Subject to any disclaimer, the term of this patent is extended or adjusted under 35 U.S.C. 154(b) by 0 days.

(21) Appl. No.: 13/575,503

(22) PCT Filed: Jan. 19, 2011

(86) PCT No.: PCT/JP2011/000234
§ 371 (c)(1),
(2), (4) Date: Aug. 27, 2012

(87) PCT Pub. No.: WO2011/093030
PCT Pub. Date: Aug. 4, 2011

(65) Prior Publication Data
US 2012/0328476 A1  Dec. 27, 2012

(30) Foreign Application Priority Data
Jan. 28, 2010 (JP) ................................ 2010-016151

(51) Int. Cl.
*G01N 21/00* (2006.01)
*G01N 35/00* (2006.01)
*G01N 35/02* (2006.01)
*G01N 35/10* (2006.01)

(52) U.S. Cl.
CPC .......... *G01N 35/025* (2013.01); *G01N 35/1002* (2013.01)
USPC .............................................. 422/64; 436/43

(58) Field of Classification Search
CPC .................. G01N 35/025; G01N 35/1002

USPC ........................................................... 422/64
See application file for complete search history.

(56) References Cited

U.S. PATENT DOCUMENTS

| 4,451,433 | A | * | 5/1984 | Yamashita et al. | ............... 422/63 |
| 5,681,530 | A | * | 10/1997 | Kuster et al. | .................... 422/63 |
| 5,902,548 | A | * | 5/1999 | Watts et al. | ...................... 422/63 |
| 6,682,704 | B2 | * | 1/2004 | Bottwein et al. | .............. 422/561 |
| 7,468,161 | B2 | * | 12/2008 | Reinhardt et al. | ............... 422/63 |

(Continued)

FOREIGN PATENT DOCUMENTS

| JP | 2000-321283 A | 11/2000 |
| JP | 2005-037171 A | 2/2005 |
| JP | 2008-203004 A | 9/2008 |
| JP | 2009-36561 A | 2/2009 |

*Primary Examiner* — Jill Warden
*Assistant Examiner* — Brittany Fisher
(74) *Attorney, Agent, or Firm* — Mattingly & Malur, PC

(57) ABSTRACT

The present invention provides an automatic analyzer for analyzing blood, urine, or other samples in which, for the purpose of reducing the workload of the operator, the process of reagent replacement is automated such that the measurement operation of the analyzer need not be halted during the reagent replacement. A sample rack transfer mechanism and reagent storage/transfer mechanisms are placed on different levels of two-story structure. This configuration allows reagent replacement even when the analyzer is performing an analysis, as well as achieving size reduction of the analyzer. The automation of reagent replacement is achieved by the following: a sensor's detection of the remaining reagent amount in a reagent vessel reaching a particular value; and the analyzer's detection of a measurement request for a sample rack when necessary reagents are not present in any reagent storage mechanism of an analyzer unit.

7 Claims, 3 Drawing Sheets

(56) References Cited

U.S. PATENT DOCUMENTS

| | | | |
|---|---|---|---|
| 2002/0164807 A1* | 11/2002 | Itaya et al. | 436/45 |
| 2004/0205783 A1* | 10/2004 | Ting et al. | 720/601 |
| 2004/0253146 A1* | 12/2004 | Shiba et al. | 422/64 |
| 2005/0047964 A1* | 3/2005 | Nishida et al. | 422/64 |
| 2005/0084426 A1* | 4/2005 | Mimura et al. | 422/102 |
| 2005/0207938 A1* | 9/2005 | Hanawa et al. | 422/64 |
| 2005/0227360 A1* | 10/2005 | Devlin, Sr. | 436/45 |
| 2008/0003137 A1* | 1/2008 | Burkhardt et al. | 422/64 |
| 2008/0199358 A1 | 8/2008 | Yamano | |
| 2008/0241939 A1* | 10/2008 | Matsuo et al. | 436/54 |
| 2009/0035867 A1* | 2/2009 | Yagi et al. | 436/50 |

* cited by examiner

AUTOMATIC ANALYZER

TECHNICAL FIELD

The present invention relates to automatic analyzers for analyzing samples such as blood and urine and particularly to an automatic analyzer involving many measurement-related steps.

BACKGROUND ART

Due to increases in the number of samples to be treated and in the number of measurement items to be examined, automatic analyzers for analyzing blood, urine, or other samples are forced to consume reagents much faster. Accordingly, reagent replacement has now to be conducted more frequently. On the other hand, there is also a growing demand for minimizing the workload of operators to decrease personnel costs.

The analyzer of Patent Document 1 below is designed to conduct reagent replacement by having a reagent storage mechanism installed on its analyzer unit.

PRIOR ART DOCUMENT

Patent Document

Patent Document 1: JP-2005-37171-A

SUMMARY OF THE INVENTION

Problem to be Solved by the Invention

As stated above, increases in the number of samples to be treated and in the number of their properties to be examined require reagent replacement to be conducted more frequently. In addition, mechanisms of an analyzer are now operated at higher speed to speed up measurement. For these reasons, reagent replacement needs to be automated such that analyzer operation need not be halted. The automation of reagent replacement is necessary in terms of personnel costs as well.

Means for Solving the Problem

To address the above issue, the present invention is designed such that the following components are placed on different levels of two-story structure: a sample rack storage mechanism for temporarily storing sample racks on a buffer mechanism; and a reagent storage mechanism for replacing reagent vessels in an analyzer unit with new ones. This configuration allows new reagent vessels for replacement to be transferred from the buffer mechanism to the analyzer unit when a sensor has detected that the remaining reagent amount in a reagent vessel in the analyzer unit has reached a given value, or when there is a measurement request involving the use of reagents that are not present in the analyzer unit. During such reagent replacement, the operation of the analyzer is not halted. In addition, the reagent storage mechanism of the buffer mechanism is formed into a circular shape, not a liner shape; thus, reagent replacement can be conducted at high speed.

Effects of the Invention

As stated above, the present invention allows automatic reagent replacement by the automatic analyzer, not manual reagent replacement by an operator, when a sensor has detected that the remaining reagent amount in a reagent vessel in the analyzer unit has reached a given value during the operation of the analyzer, or when reagents that are not present in the analyzer unit are to be used. This increases the cost-effectiveness of the analyzer. Moreover, placing the reagent storage mechanism of the buffer mechanism and the sample rack storage mechanism on different levels of two-story structure allows space-saving.

MODE FOR THE CARRYING OUT THE INVENTION

Embodiments of the present invention will now be described with reference to the accompanying drawings.

Figure 1:
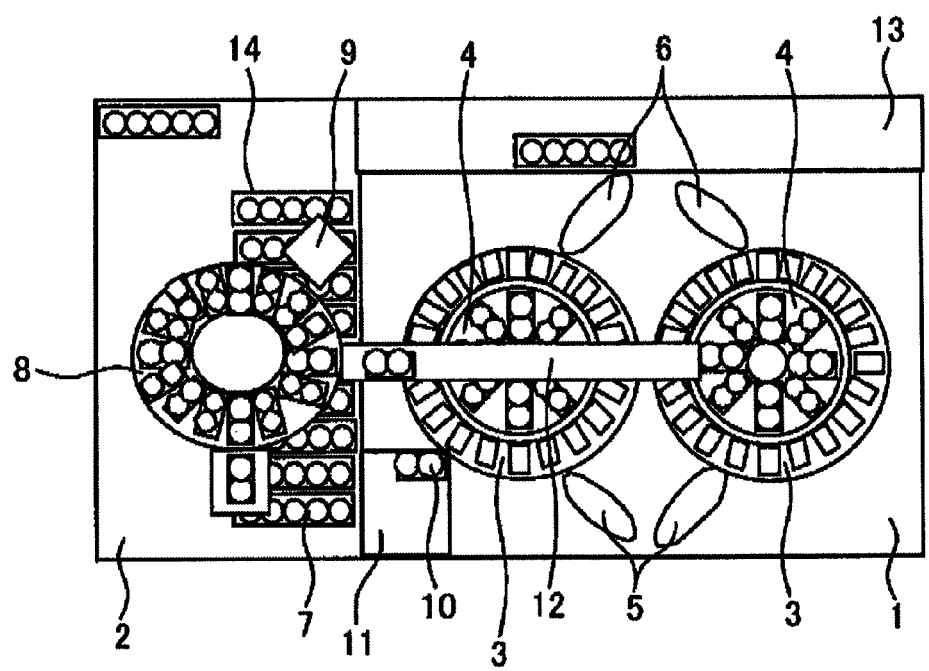
FIG. 1 is a top view illustrating an automatic analyzer according to an embodiment of the invention, the analyzer including a buffer mechanism.

FIG. 1 is a partial top view of an automatic analyzer according to an embodiment of the invention. The automatic analyzer includes an analyzer unit 1, a buffer mechanism 2, and a sample rack transfer path 13. The analyzer unit 1 includes the following components: two reaction mechanisms 3 in which samples and reagents are caused to react; and two reagent storage mechanisms 4 for storing reagent vessels at a constant temperature. Each of the reagent storage mechanisms 4 is surrounded by one of the reaction mechanisms 3, forming two rotatable, circular units. The analyzer unit 1 also includes two reagent dispensing mechanisms 5 for dispensing (i.e., suctioning and discharging) reagents stored by the analyzer unit 1 and two sample dispensing mechanisms 6 for dispensing samples. Otherwise, a reaction mechanism and a reagent storage mechanism may be arranged in different circular patterns respectively, and each of them may be provided with sample and reagent dispensing mechanisms.

The buffer mechanism 2 includes the following components: a sample rack storage mechanism 14 for temporarily storing several sample racks 7 on each of which multiple sample vessels are placed; and a reagent storage mechanism 8. The reagent storage mechanism 8 of the buffer mechanism 2 is also circular and rotates in one direction. This circular, rotatable reagent storage mechanism 8 is capable of storing multiple reagent vessels. Because reagent vessels need to be stored at a constant temperature to prevent their deterioration, the reagent storage mechanism 8 is temperature-controlled. The buffer mechanism 2 also includes an automatic registration mechanism 9 for registering the names of reagents for the purposes of validity date management and measurement.

During the operation of the automatic analyzer, the reagent dispensing mechanisms 5 installed on the analyzer unit 1 examine the remaining amount of reagents before suctioning them. When a sensor has detected that the remaining reagent amount in a reagent vessel has reached a particular value that requires replacement, that reagent vessel (placed on either one of the reagent storage mechanisms 4 of the analyzer unit 1) is transferred to a reagent vessel container 11. By detecting "that reagent vessel" is transferred to a reagent vessel container 11, a new reagent vessel is transferred from the reagent storage mechanism 8 through a reagent vessel transfer path 12 to the reagent storage mechanism 4 where the new vessel should be. Alternatively, such reagent vessel transfers at the analyzer unit 1 and at the buffer mechanism 2 can be started simultaneously, right after a sensor has detected a reagent vessel with a small reagent amount during the reagent suctioning by a reagent dispensing mechanism 5. It is to be noted that during reagent replacement, mechanisms of the automatic analyzer such as the analyzer unit 1, the buffer mechanism 2, and the sample rack transfer mechanism 13 are operated in a continuous manner without interruption.

Reagent replacement can also be done in the following manner. In the event that necessary reagent vessels for measurement are not present on the analyzer unit 1 after measurement items have been determined through the reading of the barcode of a sample rack 7, unnecessary reagent vessels are transferred from either one of the reagent storage mechanisms 4 to the reagent vessel container 11. The necessary reagent vessels are then transferred from the reagent storage mechanism 8 of the buffer mechanism 2 through the reagent vessel transfer path 12 to the reagent storage mechanism 4 of the analyzer unit 1 where the necessary ones should be. During this reagent replacement, too, the analyzer unit 1, the buffer mechanism 2, the sample rack transfer mechanism 13, and other analyzer components are continuously operated without interruption.

Figure 2:
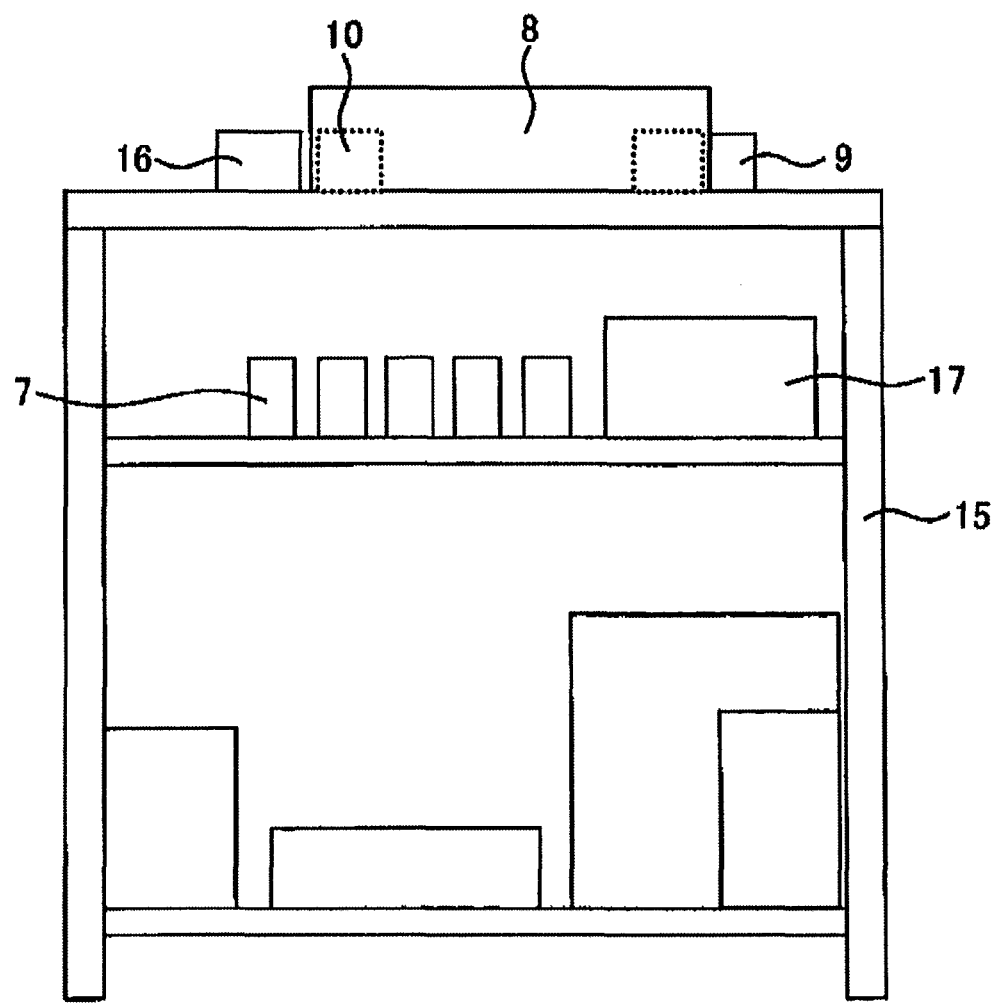
FIG. 2 is a side view of the buffer mechanism.

FIG. 2 is a side view of the buffer mechanism 2. The buffer mechanism 2 includes a buffer mechanism rack 15 which has a multi-story structure. The reagent storage mechanism 8 is installed on the top level of the rack 15, and a mechanism for storing sample racks temporarily is installed on another level of the rack 15.

Typically, the reagent transfer path and the sample rack transfer path of an automatic analyzer are placed on the same level, making its size large. The present invention, in contrast, has adopted a structure in which the reagent storage mechanism 8, the reagent transfer path 12, the sample rack storage mechanism 14, and the sample rack transfer path 13 are placed on different levels, thereby making the automatic analyzer compact. This structure also allows a reagent vessel to be transferred from the reagent storage mechanism 8 of the buffer mechanism 2 to a reagent storage mechanism 4 of the analyzer unit 1 without halting the transfer of sample racks 7. The buffer mechanism 2 also includes a reagent vessel loading unit 16 in which reagent vessels are to be placed. After a sensor has detected the placement of a reagent vessel in the loading unit 16, that vessel is loaded into the reagent storage mechanism 8. The loaded reagent vessel is then subjected to the barcode reading by the automatic registration mechanism 9, whereby the reagent is registered. The vessel that has completed the registration is put on standby until it is transferred to the analyzer unit 1. Sample racks 7 are loaded into the buffer mechanism 2 via a different mechanism. Loaded sample racks 7 are temporarily stored there until they are transferred to the analyzer unit 1. Sample racks 7 that have completed measurement at the analyzer unit 1 are transferred back to the buffer mechanism 2 for temporary storage, so that they can later be used for reanalysis. Note here that temporary storage of sample racks without any treatment may result in deterioration of the samples contained in the sample racks, affecting the results of measurement. Therefore, the buffer mechanism 2 further includes a cooling mechanism 17 at the location where sample racks 7 are stored temporarily. The reagent storage mechanism 8 of the buffer mechanism 2 is also temperature-controlled to keep a constant temperature to prevent deterioration of reagents. Because, in the present embodiment, the sample rack storage mechanism 14 and the reagent storage mechanism 8 are installed on different levels, the temperature control mechanism (i.e., the cooling mechanism 17) is installed between the two to control the temperatures of both levels.

Figure 3:
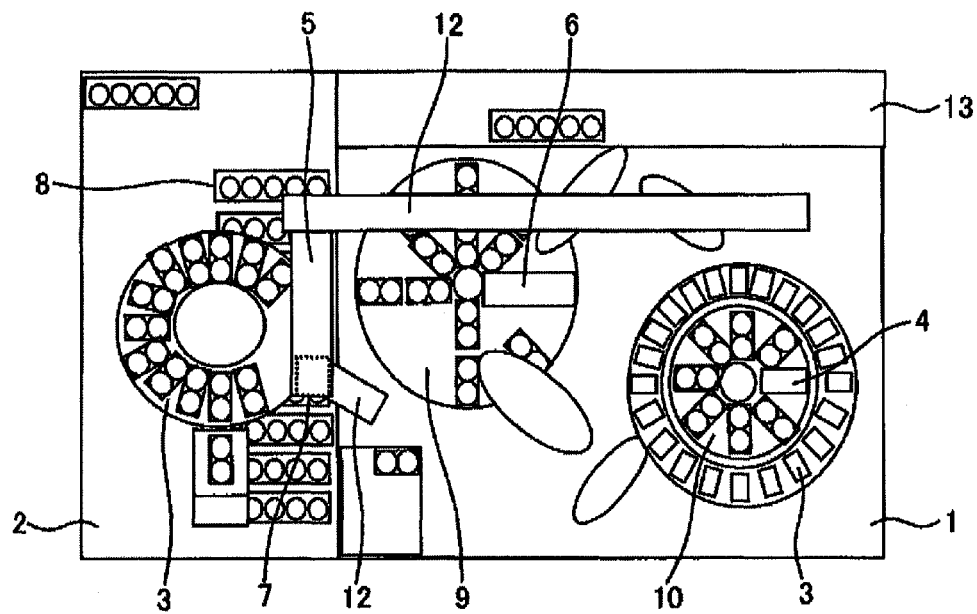
FIG. 3 is a top view of an automatic analyzer according to another embodiment of the invention.

FIG. 3 is a top view of an automatic analyzer according to another embodiment of the invention. Similar to the analyzer of FIG. 1, the analyzer of FIG. 3 includes the analyzer unit 1, the buffer mechanism 2, and the sample rack transfer path 13. The analyzer unit 1 includes two circular reagent storage mechanisms 9 and 10 and a single reaction mechanism 11. The reaction mechanism 11 is disposed so as to surround one of the reagent storage mechanisms. Note that as viewed from the top of the analyzer, the reagent storage mechanisms 9 and 10 are not coaxially aligned with each other to achieve space-saving.

The buffer unit 2 includes one circular reagent storage mechanism 3 for automatically replacing reagents stored by the analyzer unit 1. The reagent storage mechanism of the buffer mechanism 2 and the reagent storage mechanisms 9 and 10 of the analyzer unit 1 are not coaxially aligned with one another. Reagent vessel transfer mechanisms 4 and 5 are provided so as to transfer reagent vessels from the buffer mechanism 2 to the reagent storage mechanisms 9 and 10 of the analyzer unit 1.

A reagent vessel placed on the buffer mechanism 2 is moved to a holding position by a reagent vessel holding position changing mechanism 13. After the reagent vessel has been moved to the holding position, a reagent vessel holding mechanism 7 transfers the reagent vessel. During the transfer, a reagent transfer mechanism moves in X- and Y-directions. In addition, the reagent vessel holding mechanism 7 can move in a Z-direction. These movements allow transfer of reagent vessels to all the reagent storage mechanisms that are not coaxially aligned. Since reagents need to be stored at a constant temperature to prevent their deterioration, the reagent storage mechanisms of the buffer mechanism 2 and the analyzer unit 1 are temperature-controlled to keep a constant temperature. Moreover, a reagent storage mechanism opener/closer 6 is used during reagent replacement so that when reagent vessels approach the opener/closer 6, it can be opened or closed automatically, followed by the transfer of the reagent vessels to any of the reagent storage mechanism.

During the operation of the analyzer, difficulty is involved in transferring reagent vessels placed on the buffer mechanism 2 to the reagent storage mechanisms of the analyzer unit 1 because the reagent and sample dispensing mechanisms are also in operation. When a sensor has detected that the remaining reagent amount in a reagent vessel in any reagent storage mechanism of the analyzer unit 1 has reached a low value, a new reagent vessel is transferred from the buffer mechanism 2. During the transfer, the sample and reagent dispensing mechanisms are temporarily placed at standby positions so as to avoid their contact with the reagent transfer mechanism. Thereafter, the transfer mechanism holding the new reagent vessel transfers that vessel to either one of the two reagent storage mechanisms 9 and 10.

It is also possible to install a sensor on the reagent vessel holding mechanism 7 or on the reagent and sample dispensing mechanisms, so that the sensor can detect likely contact of the reagent vessel holding mechanism 7 with the reagent and sample dispensing mechanisms before it happens. Immediately after such detection, the reagent vessel holding mechanism 7 can be moved in X-, Y-, and Z-directions, or the reagent and sample dispensing mechanisms can be moved to a safe position to avoid actual contact. Finally, it is to be noted that conventional automatic analyzers have required manual replacement of reagents.

DESCRIPTION OF THE REFERENCE NUMERALS

1: Analyzer unit
2: Buffer mechanism

3: Reaction mechanism
4: Reagent storage mechanism of the analyzer unit
5: Reagent dispensing mechanism
6: Sample dispensing mechanism
7: Sample rack
8: Reagent storage mechanism of the buffer mechanism
9: Reagent barcode reader
10: Reagent vessel
11: Reagent vessel container
12: Reagent vessel transfer path
13: Sample rack transfer path
14: Sample rack storage mechanism of the buffer mechanism
15: Buffer mechanism rack
16: Reagent vessel loading unit
17: Cooling mechanism

The invention claimed is:

1. An automatic analyzer comprising:
a first reagent vessel container for storing a plurality of reagent vessels that each contain a reagent to be used for analysis;
a second reagent vessel container for storing reagent vessels to be transferred to the first reagent vessel container;
a reagent vessel transfer mechanism for transferring reagent vessels between the first reagent vessel container and the second reagent vessel container;
at least one sample dispensing mechanism for suctioning and discharging samples;
a sample rack storage mechanism for temporarily storing sample racks until the sample racks which hold samples to be used for analysis are transferred from the sample rack storage mechanism to a position adjacent to the at least one sample dispenser; and
a sample rack transfer path along which the sample racks are transferred to be adjacent to the sample dispensing mechanism,
wherein the second reagent vessel container is installed on a first level different from a second level on which a sample rack storage mechanism is installed, and the first level is higher than the second level, and
wherein the second reagent vessel container overlaps the sample rack storage mechanism in a plan view.

2. The automatic analyzer of claim 1, further comprising:
a temperature control mechanism installed between the sample rack storage mechanism and the second reagent vessel container,
wherein the temperature control mechanism controls temperatures of the sample rack storage mechanism and the second reagent vessel container.

3. The automatic analyzer of claim 1, further comprising a reagent vessel transfer path for transferring reagent vessels from the second reagent vessel container to the first reagent vessel container,
wherein the first reagent vessel container and the second reagent vessel container are circular respectively, and the first reagent vessel container and the second reagent vessel container are placed so that a line across the reagent vessel transfer path passes through a center of the first reagent vessel container and a center of the second reagent vessel container.

4. The automatic analyzer of claim 1, wherein two of the first reagent vessel containers are installed, the reagent vessels are transferred to either one of the first reagent vessel containers.

5. The automatic analyzer of claim 1, further comprising:
a sample dispensing mechanism for suctioning and discharging samples;
a reagent dispensing mechanism for suctioning and discharging reagents;
a reagent vessel holding mechanism for holding the reagent vessels; and
a sensor installed on the reagent vessel holding mechanism or on the reagent and sample dispensing mechanisms,
wherein the reagent vessel holding mechanism or the reagent and sample dispensing mechanisms move to a position to avoid actual contact when the sensor detects likely contact of the reagent vessel holding mechanism with the reagent and sample dispensing mechanisms.

6. The automatic analyzer of claim 1,
wherein the first reagent vessel container and the second reagent vessel container are installed on different levels, with the second reagent vessel container being placed on a higher level than the first reagent vessel container.

7. The automatic analyzer of claim 4, further comprising:
a sample dispensing mechanism for suctioning and discharging samples; and
a reagent dispensing mechanism for suctioning and discharging reagents,
wherein the reagent and sample dispensing mechanisms temporarily move to standby positions when the reagent vessels are transferred to either one of the first reagent vessel containers.

* * * * *